US012605340B2

(12) United States Patent
Daud et al.

(10) Patent No.: US 12,605,340 B2

(45) Date of Patent: Apr. 21, 2026

(54) EXTENDED RELEASE COMPOSITION OF 2-(2-AMINOTHIAZOL-4-YL)-N-[4-(2{[(2R)-2-HYDROXY-2-PHENYLETHYL] AMINO} ETHYL) PHENYL] ACETAMIDE

(71) Applicant: Zim Laboratories Limited, Maharashtra (IN)

(72) Inventors: Anwar Daud, Maharashtra (IN); Chandrashekhar Mainde, Maharashtra (IN); Uttam Kedar, Maharashtra (IN); Kuldeep Gangawat, Maharashtra (IN)

(73) Assignee: ZIM LABORATORIES LIMITED, Maharashtra (IN)

(*) Notice: Subject to any disclaimer, the term of this patent is extended or adjusted under 35 U.S.C. 154(b) by 609 days.

(21) Appl. No.: 17/922,914

(22) PCT Filed: May 15, 2021

(86) PCT No.: PCT/IB2021/054184

§ 371 (c)(1),
(2) Date: Nov. 2, 2022

(87) PCT Pub. No.: WO2021/234526

PCT Pub. Date: Nov. 25, 2021

(65) Prior Publication Data

US 2023/0157962 A1 May 25, 2023

(30) Foreign Application Priority Data

May 17, 2020 (IN) ............................. 202021020771

(51) Int. Cl.

| | |
|---|---|
| ***A61K 9/16*** | (2006.01) |
| ***A61K 9/20*** | (2006.01) |
| ***A61K 9/28*** | (2006.01) |
| ***A61K 31/426*** | (2006.01) |

(52) U.S. Cl.

CPC ............ *A61K 9/284* (2013.01); *A61K 9/2009* (2013.01); *A61K 9/2013* (2013.01); *A61K 9/2018* (2013.01); *A61K 9/2027* (2013.01); *A61K 9/2813* (2013.01); *A61K 9/288* (2013.01); *A61K 31/426* (2013.01)

(58) Field of Classification Search

None

See application file for complete search history.

(56) References Cited

U.S. PATENT DOCUMENTS

| | | | | |
|---|---|---|---|---|
| 8,877,214 | B2 | 11/2014 | Takaishi et al. | |
| 2017/0128379 | A1* | 5/2017 | Pilgaonkar | A61K 9/5047 |

FOREIGN PATENT DOCUMENTS

| | | | | | |
|---|---|---|---|---|---|
| CA | 3078568 | A1 * | 4/2019 | | A61K 31/426 |
| EP | 2554168 | A1 | 2/2013 | | |
| EP | 3292864 | A1 | 3/2018 | | |
| KR | 2018/0104259 | A | 9/2018 | | |
| KR | 2018/0106238 | A | 10/2018 | | |
| KR | 20190089758 | A * | 7/2019 | | |
| KR | 20190108015 | A * | 9/2019 | | A61K 47/56 |

OTHER PUBLICATIONS

International Search Report and Written Opinion for PCT/IB2021/054184, dated Sep. 6, 2021, 7 pgs.

* cited by examiner

*Primary Examiner* — Susan T Tran

(74) *Attorney, Agent, or Firm* — BLANK ROME LLP

(57) ABSTRACT

The present invention relates to extended release composition of Mirabegron and process of manufacture thereof. The extended release composition of mirabegron comprising non-polymeric hydrophobic excipient as release controlling agent along with one or more pharmaceutically acceptable excipient is used in the treatment of symptoms associated with overactive bladder.

6 Claims, 1 Drawing Sheet

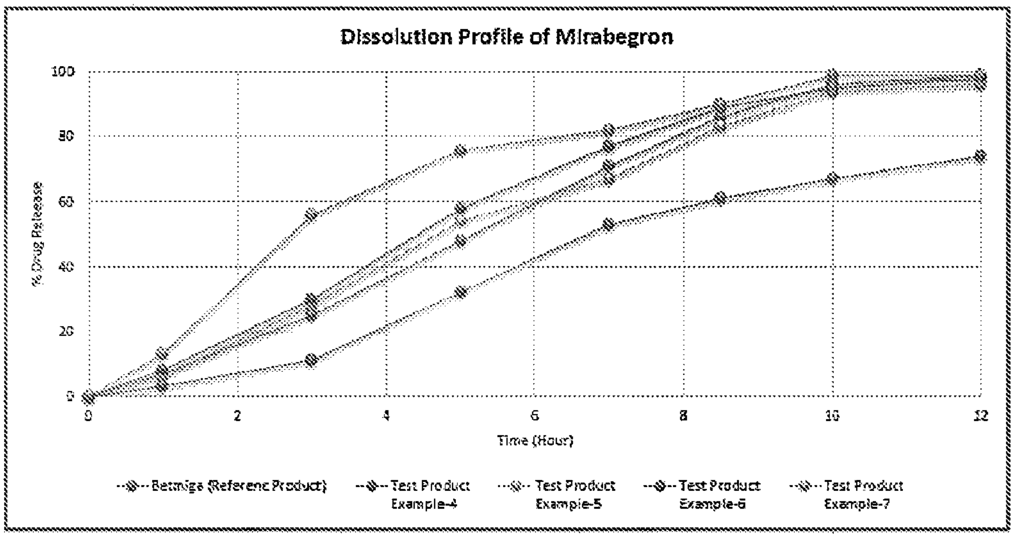
Dissolution Profile of Mirabegron
% Drug Release
Time (Hour)
Betmiga (Referenc Product)
Test Product Example-4
Test Product Example-5
Test Product Example-6
Test Product Example-7

EXTENDED RELEASE COMPOSITION OF 2-(2-AMINOTHIAZOL-4-YL)-N-[4-(2{[(2R)-2-HYDROXY-2-PHENYLETHYL] AMINO} ETHYL) PHENYL] ACETAMIDE

This application is a national stage of International Application No. PCT/IB2021/054184, filed on May 15, 2021, which claims priority to Indian Patent Application No. 202021020771, filed on May 17, 2020. The contents of these applications are hereby incorporated by reference in their entireties.

FIELD OF THE INVENTION

The present invention relates to extended release composition of 2-(2-Aminothiazol-4-yl)-N-[4-(2-{[(2R)-2-Hydroxy-2-Phenylethyl]Amino}Ethyl)Phenyl] Acetamide or salt thereof (Mirabegron or salt thereof) and process of manufacture thereof. Specifically, the present invention relates to extended release composition comprising Mirabegron and non-polymeric hydrophobic excipient as extended release agent.

BACKGROUND OF THE INVENTION

Overactive bladder (OAB) is a condition where there is a frequent feeling of needing to urinate to a degree that it negatively affects a person's life. The frequent need to urinate may occur during the day, at night, or both. If there is loss of bladder control then it is known as urge incontinence. More than 40% of people with overactive bladder have incontinence. Conversely, about 40% to 70% of urinary incontinence is due to overactive bladder. The cause of overactive bladder is unknown. Risk factors include obesity, caffeine, and constipation. Poorly controlled diabetes, poor functional mobility, and chronic pelvic pain may worsen the symptoms. Overactive bladder is characterized by symptoms like urgency, urinary frequency, nocturia, and urge incontinence.

Treatment for Overactive bladder includes nonpharmacologic methods such as lifestyle modification, bladder retraining, and pelvic floor muscle (PFM) exercise. A number of antimuscarinic drugs like darifenacin, hyoscyamine, oxybutynin, tolterodine, solifenacin, trospium, fesoterodine used to treat overactive bladder. β3 adrenergic receptor agonists mirabegron, vibegron are also used in the treatment of Overactive bladder.

Mirabegron is a beta-3 adrenergic agonist. The chemical name of mirabegron is 2(2-aminothiazol-4-yl)-N-[4-(2-{[(2R)-2-hydroxy2phenyl ethyl]amino}ethyl)phenyl] acetamide. Its empirical formula is $C_{21}H_{24}N_4O_2S$ and a molecular weight is of 396.51. Mirabegron represented by structural formula (I)

Formula (I)

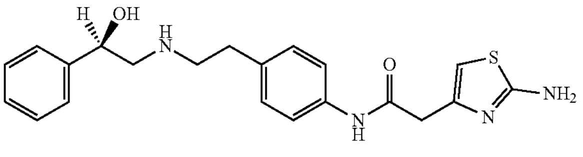

Mirabegron is a white powder. It is practically insoluble in water. It is soluble in methanol and dimethyl sulfoxide.

Mirabegron Extended release tablet [25 mg & 50 mg] is approved under the tradename Myrbetriq® in USA & Betmiga® in Europe. The product is indicated for the treatment of Overactive bladder in adult patients with symptoms of urge urinary incontinence, urgency, and urinary frequency.

The Mirabegron Extended release tablet under the trade name Myrbetriq®/Betmiga® contain 25 mg or 50 mg of Mirabegron and the following inactive ingredients: polyethylene oxide, polyethylene glycol, hydroxypropyl cellulose, butylated hydroxytoluene, magnesium stearate, hypromellose, yellow ferric oxide, and red ferric oxide.

The marketed Myrbetriq®/Betmiga® tablet based on Oral Controlled Absorption System (OCAS) modified release platform. The OCAS is a hydrophilic gel-forming matrix tablet formulation, composed of active substance and Macrogols. This matrix tablet formulation designed for continuous drug release in the human GI tract.

The European patent EP2554168B1 discloses composition of extended release with different technologies. The said patent publication discloses, a sustained release hydrogel-forming formulation, a multi-layered formulation consisting of a drug core and a release-controlling layer, a gel formulation in which a plurality of gums is combined, an osmotic pump type formulation, a formulation utilizing a swelling polymer, a matrix formulation utilizing a water-soluble polymer, a modified release formulation with a coating membrane, and a matrix formulation utilizing an insoluble polymer. Further, EP2554168B1 discloses a matrix formulation utilizing an insoluble polymer, wherein the drug is uniformly dispersed in a water-insoluble polymer. Because the matrix consisting of the water-insoluble polymer can control the penetration of water into the formulation, the matrix formulation can modify the release of the drug from the formulation by controlling the dissolution rate of the drug in the matrix and the dispersion rate of the dissolved drug in the matrix. The said patent generically discloses water insoluble polymer like carnauba wax, cetyl alcohol, and glyceryl behenate. However, said patent does not teaches or discloses specific use of said polymers with mirabegron. Also does not provide any illustration with specific example to observe behavior of said excipients with mirabegron.

The U.S. Pat. No. 8,877,214 disclose the Mirabegron formulation of different technologies. It also covers drug core and a release-controlling layer, a gel formulation in which a plurality of gums combined, an osmotic pump type formulation, a formulation utilizing a swelling polymer, a matrix formulation utilizing a water-soluble polymer, a modified release formulation with a coating membrane, and a matrix formulation utilizing an insoluble polymer.

The European patent EP3292864 disclose a modified release tablet composition comprising Mirabegron and manufacture process thereof. In the description of said patent, generically discloses composition of the invention may also contain a lubricant. Lubricants are generally used in order to reduce sliding friction. Suitable lubricants to be used include magnesium stearate, calcium stearate, stearic acid, glyceryl behenate, hydrogenated vegetable oil, and glycerin fumarate.

Commercially available product and product known in the prior art for Mirabegron modified release tablet contains use of OCAS system. The OCAS is a hydrophilic gel-forming matrix tablet formulation, composed of active substance and Macrogols. Oral Controlled-Absorption System is a drug delivery technology enabling the gradual release of drug active through the tablet; however, applicant of the present invention prepared the extended release composition of Mirabegron without using the OCAS system and achieving the similar in vitro release profile as that of formulation prepared according to the OCAS system under the trade name Myrbetriq®/Betmiga®.

Accordingly, applicant of the present invention invented novel extended release composition of Mirabegron comprising non-polymeric hydrophobic excipients as release controlling agent, which is stable and provide optimum release of drug from the dosage form in the treatment of overactive bladder in adult patients with symptoms of urge urinary incontinence, urgency, and urinary frequency.

OBJECT OF THE INVENTION

Accordingly, it is an object of the present invention is to provide extended release composition of Miraberon comprising non-polymeric hydrophobic excipients as release controlling agent.

It is another object of the present invention is to provide extended release composition comprising Miraberon and non-polymeric hydrophobic excipients selected from the group consisting of glyceryl behenate, carnauba wax and cetyl alcohol, hydrogenated vegetable oil, hydrogenated castor oil, stearic acid and like or mixture therefore.

It is another object of the present invention is to provide extended release composition comprising Miraberon and non-polymeric hydrophobic excipient as release controlling agent selected from the group consisting of glyceryl behenate, carnauba wax and cetyl alcohol, hydrogenated vegetable oil, hydrogenated castor oil, stearic acid and like or mixture therefore.

It is another object of the present invention is to provide extended release composition comprising Miraberon, non-polymeric hydrophobic excipient as release controlling agent along with one or more pharmaceutically acceptable excipient.

It is another object of the present invention is to provide extended release composition comprising Miraberon, non-polymeric hydrophobic excipient as release controlling agent along with one or more pharmaceutically acceptable excipient in the form of tablet, capsule, sachet, granules, beads, pellets or powder.

It is another object of the present invention is to provide process of manufacturing extended release composition comprising Miraberon, non-polymeric hydrophobic excipient as release controlling agent along with one or more pharmaceutically acceptable excipient.

It is another object of the present invention is to provide extended release composition comprising Miraberon, non-polymeric hydrophobic excipient as release controlling agent, along with one or more pharmaceutically acceptable excipient in treatment of overactive bladder in adult patients with symptoms of urge urinary incontinence, urgency, and urinary frequency.

SUMMARY OF THE INVENTION

The present invention relates to extended release composition of Mirabegron and process of manufacture thereof. The present invention relates to extended release composition comprising Mirabegron and non-polymeric hydrophobic excipients as release controlling agent. The non-polymeric hydrophobic excipients are selected from the consisting of glyceryl behenate, carnauba wax and cetyl alcohol, hydrogenated vegetable oil, hydrogenated castor oil, stearic acid and like or mixture therefore. The extended release composition comprising Mirabegron, non-polymeric hydrophobic excipients as release controlling agent along with one or more pharmaceutically acceptable excipient is stable and provides in vitro dissolution similar to the commercially available product under brand Myrbetriq®/Betmiga®. Therefore extended release composition of Mirabegron provides patient compliance in the treatment of overactive bladder in adult patients with symptoms of urge urinary incontinence, urgency, and urinary frequency.

BRIEF DESCRIPTION OF ACCOMPANYING FIGURES

FIG. 1: Illustrates the comparison of dissolution profile of Mirabegron Extended release composition test product (Examples 1, 2, 3, 4) and reference product under trade name Betmiga®

DETAILED DESCRIPTION OF THE INVENTION

The present invention relates to extended release composition of 2-(2-Aminothiazol-4-yl)-N-[4-(2-{[(2R)-2-Hydroxy-2-Phenylethyl]Amino}Ethyl)Phenyl] Acetamide or salt thereof and process of manufacture thereof.

The common name for 2-(2-Aminothiazol-4-yl)-N-[4-(2-{[(2R)-2-Hydroxy-2-Phenylethyl]Amino}Ethyl)Phenyl] Acetamide or salt thereof is Mirabegron or salt therefore. Therefore, hereinafter 2-(2-Aminothiazol-4-yl)-N-[4-(2-{[(2R)-2-Hydroxy-2-Phenylethyl]Amino}Ethyl)Phenyl] Acetamide is referred as mirabegron.

The term "extended release composition" as used herein means a formulation in which the dissolution rate of the drug from the formulation is less than 85% after 30 minutes from the beginning a dissolution test. The dissolution test is carried out under in accordance with a dissolution test (paddle method) described in the United States Pharmacopoeia under the conditions that 900 mL of an appropriate test fluid (such as a USP buffer, pH 6.8) is used and the paddle rotation speed is 100 rpm.

The term "extended release" according to present invention can be used interchangeably with "sustained release", "slow release", "controlled release", "modified release" or "long term release".

The term composition or formulation according to present invention are similar and can be used interchangeably. The term composition according to present invention is intended to encompass at least one active ingredient, and at least one pharmaceutical acceptable excipient.

The active ingredient Mirabegron may be used in the composition in its free base form or pharmaceutically acceptable salt. The Mirabegron may be used in its acid addition salt. Examples of such a salt include an acid addition salt with hydroiodic acid, nitric acid, hydrochloric acid, hydrobromic acid, sulfuric acid, citric acid, phosphoric acid, formic acid, acetic acid, propionic acid, oxalic acid, malonic acid, succinic acid, fumaric acid, maleic acid, lactic acid, malic acid, tartaric acid, carbonic acid, picric acid, methanesulfonic acid, ethanesulfonic acid, glutamic acid or the like.

In another embodiment of the present invention is to provide extended release composition of Miraberon comprising non-polymeric hydrophobic excipients as release controlling agent.

The release controlling non-polymeric hydrophobic excipients may be selected from the group consisting of Glyceryl behenate, carnauba wax, cetyl alcohol, hydrogenated vegetable oil, hydrogenated castor oil, stearic acid and like or mixture therefore. The extended release non-polymeric hydrophobic excipients are water insoluble and non-swellable. These excipients contribute to extend the release of drug from the dosage form through diffusion and erosion mechanism.

The extended release composition comprising Miraberon, non-polymeric hydrophobic excipient as release controlling agent according to present invention may be in the form of tablet, capsule, sachet, granules, beads, pellets or powder.

In another embodiment of the present invention is to provide extended release composition comprising Miraberon, non-polymeric hydrophobic excipient as release controlling agent along with one or more pharmaceutically acceptable excipient.

The term pharmaceutically acceptable excipient means a pharmacologically inactive component. The excipient(s) that are useful in preparing a pharmaceutical composition are generally safe, non-toxic and are acceptable for human as well as veterinary pharmaceutical use.

The one or more pharmaceutically acceptable excipient according to present invention may be selected from the group consisting of diluents, release controlling agent, surfactant, antioxidants, binders, disintegrant, lubricant, anti-tacking agents, plasticizers, opacifiers, coating polymers or solvents or combination thereof and alike.

The diluent include but not limited to mannitol, lactose, microcrystalline cellulose, sugar, dextrates, dextrin, dextrose, fructose, lactitol, sucrose, starch, xylitol, sorbitol, talc, calcium carbonate, calcium phosphate dibasic or tribasic, calcium sulphate, or combination thereof and alike. The most preferably diluents are Lactose and Mannitol. The composition according to present invention contains diluent from 15 to 80% by weight of composition.

The release controlling agent according to present invention are non-polymeric hydrophobic excipient, which have ability to control release or support to retard release. The extended release agent include but not limited to Glyceryl behenate, carnauba wax, cetyl alcohol, hydrogenated vegetable oil, hydrogenated castor oil and stearic acid. The most preferably release controlling agent is Glyceryl behenate, carnauba wax, cetyl alcohol. The composition according to present invention contains release-controlling agent from 0.5 to 50% by weight of composition. Preferably, release-controlling agent are in the range of 10 to 40% by weight of composition.

The surfactant include but not limited to sodium lauryl sulfate, sodium dodecylsulfate poloxamers, heptadecaethylene oxycetanol, lecithins, sorbitol monooleate, polyoxyethylene sorbitol monooleate, polyoxyethylene stearate, polyoxyethylen sorbitan monolaurate, polysorbates, sorbitan mono-palmitate, sodium salts of sulfosuccinates such as sodium dioctylsulfosuccinate, partially esters of fatty acids with alcohols such as glycerine monostearate, partially esters of fatty acids with sorbitans such as sorbitan monolaurate, partially esters of fatty acids with polyhydroxyethylene sorbitans such as polyethyleneglycol sorbitan monolaurate, -monostearate or -monooleate, ethers of fatty alcohols with polyhydroxyethylene, esters of fatty acids with polyhydroxyethylene, copolymers of ethylenoxide and propylenoxide and ethoxylated triglycerides or tyloxapol. The most preferably solubilizer or surfactant is sodium lauryl sulfate. The composition according to present invention contains solubilizer or surfactant from 0.5 to 10% by weight of composition; preferably 0.5 to 5% by weight of composition. The surfactant used in the composition according to present invention helps in solublization of drug and it helps in penetration of water in to the pharmaceutical composition.

The term "Antioxidants" herein refers to those compounds that, inhibit oxidation and added to prevent deterioration due to oxidation process. The antioxidant(s) is selected form the group consisting of butylated Hydroxytoluene, butylated Hydroxyanisole, ascorbic acid, tocopherol, sodium ascorbate, propyl gallate or combination thereof and alike. Preferably, antioxidants are butylated Hydroxytoluene, butylated Hydroxyanisole and propyl gallate. The composition according to present invention contains antioxidant from 0.02 to 0.3% by weight of composition.

The binder include but not limited to Povidone, starch; celluloses such as hydroxypropyl cellulose, hydroxyethyl cellulose, hydroxypropyl methylcellulose, ethyl cellulose, sodium carboxy methylcellulose; natural gums like acacia, alginic acid, guar gum; liquid glucose, dextrin, povidone, syrup, polyethylene oxide, poly-N-vinyl amide, polyethylene glycol, gelatin, poly propylene glycol, tragacanth or combination thereof and alike. Preferably, binder is povidone. The composition according to present invention contains binder from 0.5 to 20% by weight of composition.

The disintegrant include but not limited to crosspovidone, sodium starch glycolate, croscarmellose sodium, Kollidon, magnesium aluminum silicate, Chitin, Mannitol, Crosslinked alginic acid, Crosslinked starch, Calcium silicate or combination thereof and alike. The composition according to present invention contains disintegrant from 2.0 to 10.0% by weight of composition.

The Lubricant include but not limited to magnesium, aluminum or calcium or zinc stearate, stearic acid, polyethylene glycol and talc or combination thereof and alike. Preferably, lubricant is magnesium stearate. The composition according to present invention contains lubricant from 0.1 to 1% by weight of composition.

The plasticizer include but not limited to Waxes, Triethyl citrate, triacetin, Polyethylene glycol, Propylene glycol or combination thereof and alike. Preferably, plasticizer is Triethyl citrate. The formulation according to present invention contains from 0.1-5% by weight of plasticizer.

The term "Anti-tacking Agent" is a necessary component in a coating system to prevent tackiness of the dosage forms during the manufacturing process. The anti-tacking agent(s) is selected form the group consisting of talc, silicon dioxide, simethicone, glycerol monosterate or combination thereof and alike Preferably, anti-tacking agents are talc and silicon dioxide. The pharmaceutical composition contains from 1-5% by weight of anti-tacking agent(s).

The term "Opacifier(s)" used to give more pastel color and increase film coverage. They can provide white coat or mask the color of the tablet/pellet/granule core. These are mostly inorganic material. Opacifier is titanium dioxide, yellow iron oxide. Preferably, opacifier is titanium dioxide. The formulation according to present invention contains from 0.2 to 5% by weight of opacifier.

The coating polymer(s) selected from the group consisting of, polyvinyl alcohol, povidone or combination thereof and alike. The pharmaceutical composition contains from 2 to 10% by weight of coating polymer(s).

Solvents are chemical substances that can dissolve, suspend or extract other materials usually without chemically changing either the solvents or the other materials. Solvents can be organic or inorganic. They used to enhance solubility, taste, anti-microbial effectiveness or stability, to reduce dose volume or to optimize insolubility. Solvents also used to help the final product in achieving proper consistency. The solvent is selected form the group consisting of isopropyl alcohol, dichloromethane, Acetone and Purified water or combination thereof and alike.

In another embodiment of the present invention is to provide extended release composition comprising a) Miraberon or salt thereof
b) Non-polymeric hydrophobic excipient as release controlling agent selected from the group consisting of Glyceryl behenate, carnauba wax, cetyl alcohol, hydrogenated vegetable oil, hydrogenated castor oil and stearic acid.
c) Optionally one or more other pharmaceutically acceptable excipient In another embodiment of the present invention is to provide extended release composition comprising a) Miraberon or salt thereof
b) Non-polymeric hydrophobic excipient as release controlling agent selected from the group consisting of Glyceryl behenate, carnauba wax, cetyl alcohol, hydrogenated vegetable oil, hydrogenated castor oil and stearic acid.
c) Diluent selected from the group consisting of lactose, mannitol or mixture thereof
d) Optionally one or more other pharmaceutically acceptable excipient In another embodiment of the present invention is to provide extended release composition comprising a) Miraberon or salt thereof
b) Non-polymeric hydrophobic excipient as release controlling agent selected from the group consisting of Glyceryl behenate, carnauba wax, cetyl alcohol, hydrogenated vegetable oil, hydrogenated castor oil and stearic acid.
c) Antioxidant selected from the group consisting of butylated Hydroxytoluene, butylated Hydroxyanisole and propyl gallate or mixture thereof
d) Optionally one or more other pharmaceutically acceptable excipient In another embodiment of the present invention is to provide extended release composition comprising a) Miraberon or salt thereof
b) Non-polymeric hydrophobic excipient as release controlling agent selected from the group consisting of Glyceryl behenate, carnauba wax, cetyl alcohol, hydrogenated vegetable oil, hydrogenated castor oil and stearic acid.
c) binder selected from the group consisting of povidone, hydroxypropyl cellulose, starch or mixture thereof
d) Optionally one or more other pharmaceutically acceptable excipient In another embodiment of the present invention is to provide extended release composition comprising a) Miraberon or salt thereof
b) Non-polymeric hydrophobic excipient as release controlling agent selected from the group consisting of Glyceryl behenate, carnauba wax, cetyl alcohol, hydrogenated vegetable oil, hydrogenated castor oil and stearic acid.
c) Diluent selected from the group consisting of lactose, mannitol or mixture thereof
d) binder selected from the group consisting of povidone, hydroxypropyl cellulose, starch or mixture thereof
e) Optionally one or more other pharmaceutically acceptable excipient In another embodiment of the present invention is to provide extended release composition comprising a) Miraberon or salt thereof
b) Non-polymeric hydrophobic excipient as release controlling agent selected from the group consisting of Glyceryl behenate, carnauba wax, cetyl alcohol, hydrogenated vegetable oil, hydrogenated castor oil and stearic acid.
c) Diluent selected from the group consisting of lactose, mannitol or mixture thereof
d) Antioxidant selected from the group consisting of butylated Hydroxytoluene, butylated Hydroxyanisole and propyl gallate or mixture thereof
e) Optionally one or more other pharmaceutically acceptable excipient In another embodiment of the present invention is to provide extended release composition comprising a) Miraberon or salt thereof
b) Non-polymeric hydrophobic excipient as release controlling agent selected from the group consisting of Glyceryl behenate, carnauba wax, cetyl alcohol, hydrogenated vegetable oil, hydrogenated castor oil and stearic acid.
c) Antioxidant selected from the group consisting of butylated Hydroxytoluene, butylated Hydroxyanisole and propyl gallate or mixture thereof
d) binder selected from the group consisting of povidone, hydroxypropyl cellulose, starch or mixture thereof
e) Optionally one or more other pharmaceutically acceptable excipient In another embodiment of the present invention is to provide extended release composition comprising a) Miraberon or salt thereof
b) release controlling agent selected from the group consisting of Glyceryl behenate, carnauba wax, cetyl alcohol or mixture therefore
c) Lactose or mannitol or mixture thereof
d) Optionally one or more other pharmaceutically acceptable excipient.

In another embodiment of the present invention is to provide extended release composition comprising a) Miraberon or salt thereof
b) release controlling agent selected from the group consisting of Glyceryl behenate, carnauba wax, cetyl alcohol or mixture therefore
c) Povidone
d) Optionally one or more other pharmaceutically acceptable excipient.

In another embodiment of the present invention is to provide extended release composition comprising a) Miraberon or salt thereof
b) release controlling agent selected from the group consisting of Glyceryl behenate, carnauba wax, cetyl alcohol or mixture therefore
c) butylated Hydroxytoluene
d) Optionally one or more other pharmaceutically acceptable excipient.

In another embodiment of the present invention is to provide extended release composition comprising a) Miraberon or salt thereof
b) release controlling agent selected from the group consisting of Glyceryl behenate, carnauba wax, cetyl alcohol or mixture therefore c) Lactose or mannitol or mixture thereof
d) Povidone
e) butylated Hydroxytoluene
f) Optionally one or more other pharmaceutically acceptable excipient.

In another embodiment of the present invention is to provide extended release composition comprising
a) Miraberon or salt thereof
b) release controlling agent selected from the group consisting of Glyceryl behenate, carnauba wax, cetyl alcohol or mixture therefore
c) Lactose or mannitol or mixture thereof
d) Povidone
e) butylated Hydroxytoluene
f) sodium lauryl sulfate
g) colloidal anhydrous silica
h) magnesium stearate
i) Optionally film coating In another embodiment of the present invention is to provide process of manufacturing extended release composition comprising
a) Miraberon or salt thereof
b) Non-polymeric hydrophobic excipient as release controlling agent selected from the group consisting of Glyceryl behenate, carnauba wax, cetyl alcohol, hydrogenated vegetable oil, hydrogenated castor oil and stearic acid.
c) Optionally one or more other pharmaceutically acceptable excipient In another embodiment of the present invention is to provide process of manufacturing extended release composition of Miraberon or salt thereof wherein step comprises
a) Dry mixing mirabegron or salt thereof, release controlling agent, optionally along with one or more excipient
b) Granulating the dry mix of step a) optionally along with binder, antioxidant or mixture thereof
c) Heat the blend of step b) to get molted mass
d) Cool the molted mass, mill to get pellet or granules
e) Mix the granule or pellet formed in step d) optionally with one or more excipient
f) Compress the mixture of step e) to form the tablet or fill the mixture in to the capsule or sachet.

In another embodiment of the present invention is to provide process of manufacturing extended release composition of Miraberon or salt thereof wherein step comprises
a) Dry mixing mirabegron or salt thereof, Glyceryl Dibehenate, lactose Monohydrate, Sodium lauryl sulphate
b) Granulating the dry mix of step a) with povidone, butylated Hydroxytoluene
c) Heat the blend of step b) to get molted mass
d) Cool the molted mass, mill to get pellet or granules
e) Mix the granule or pellet formed in step d) optionally with one or more excipient
f) Compress the mixture of step e) to form the tablet or fill the mixture in to the capsule or sachet.

In another embodiment of the present invention is to provide process of manufacturing extended release composition of Miraberon or salt thereof wherein step comprises
a) Dry mixing mirabegron or salt thereof, Glyceryl Dibehenate, lactose Monohydrate, Sodium lauryl sulphate
b) Granulating the dry mix of step a) with povidone, butylated Hydroxytoluene
c) Heat the blend of step b) to get molted mass
d) Cool the molted mass, mill to get pellet or granules
e) Mix the granule or pellet formed in step d) with Mannitol, Colloidal anhydrous silica & Magnesium stearate f) Compress the mixture of step e) to form the tablet or fill the mixture in to the capsule or sachet.

In another embodiment of the present invention is to provide, the extended release composition comprising Miraberon, non-polymeric hydrophobic excipient as release controlling agent along with one or more pharmaceutically acceptable excipient; wherein dissolution of mirabegron from the composition is 70% or less in 1 hour. The dissolution measured in vitro in USP Apparatus Type 2 (Paddle) using pH 6.8-phosphate buffer of 900 mL, at 100 rpm.

In another embodiment of the present invention is to provide, the extended release composition comprising Miraberon, non-polymeric hydrophobic excipient as release controlling agent along with one or more pharmaceutically acceptable excipient; wherein dissolution of mirabegron from the composition is not less than 20% in 3 hours and not less than 50% in 7 hours. The dissolution measured in vitro in USP Apparatus Type 2 (Paddle) using pH 6.8-phosphate buffer of 900 mL, at 100 rpm The extended release composition comprising Miraberon, non-polymeric hydrophobic excipient as release controlling agent along with one or more pharmaceutically acceptable excipient provides similar in-vitro drug release profile as that of commercially available Myrbetriq®/Betmiga® extended release tablet. Therefore, composition according to present invention is found to be in compliance.

The extended release composition comprising Miraberon according to present invention, wherein non-polymeric hydrophobic excipient as release controlling agent are water insoluble and non-swellable. These hydrophobic excipient extend the release of drug from dosage form predominantly via diffusion and Erosion mechanism. The concentration gradient between the release medium and dosage form drives the drug out into release medium. On the other hand non swellable matrix erodes and expose the drug particles to the outside medium resulting into drug release. Through said release mechanism, extended release composition comprising Miraberon according to present invention provides optimum release in the treatment of overactive bladder in adult patients with symptoms of urge urinary incontinence, urgency, and urinary frequency.

In another embodiment of the present invention is to provide the stable extended release composition comprising Miraberon, non-polymeric hydrophobic excipient as release controlling agent along with one or more pharmaceutically acceptable excipient. The extended release composition of mirabegron according to present invention were loaded for stability study at condition of 40° C./75% RH as per ICH guideline. After stability study, in-vitro drug release profile, assay, related substances and other parameters found to be in the compliance; therefore, composition according to the invention is found to be stable.

The extended release composition comprising Miraberon, non-polymeric hydrophobic excipient as release controlling agent along with one or more pharmaceutically acceptable excipient packaged in suitable airtight containers and moisture proof packs. The pharmaceutical composition of the present invention preferably packaged in to the strip, blister, bottle or sachet.

EXAMPLE

The following Examples are provided solely for illustrative purposes and are not meant to limit the invention in any way. Some illustrative non-limiting examples of the present invention as described below.

TABLE 1

| Examples 1 to 3 | | | |
|---|---|---|---|
| Material Name | Example-1 (In mg) | Example-2 (In mg) | Example-3 (In mg) |
| TABLET CORE | | | |
| Mirabegron | 50 | 50 | 50 |
| Glyceryl dibehanate | 100 | 25 | 25 |
| Carnauba Wax | — | 20 | 20 |
| Cetyl Alcohol | — | — | 5 |
| Lactose Monohydrate | 20 | 20 | 20 |
| Crospovidone | 5 | 5 | 5 |
| Lactose Monohydrate | 107.6 | 162.6 | 157.6 |
| Butylated Hydroxy toluene | 0.4 | 0.4 | 0.4 |
| Crospovidone | 10 | 10 | 10 |
| Colloidal Anhydrous Silica | 5 | 5 | 5 |
| Magnesium stearate | 2 | 2 | 2 |
| Total weight | 300 | 300 | 300 |
| FILM COATING | | | |
| Povidone/Polyvinyl alcohol | 10.5 | 10.5 | 10.5 |
| Carnauba Wax | 1.5 | 1.5 | 1.5 |
| Talcum | 2.5 | 2.5 | 2.5 |
| Titanium dioxide | 1.5 | 1.5 | 1.5 |
| Solvent | Qs | Qs | Qs |
| Total weight | 316 | 316 | 316 |

Manufacturing Procedure

1) Dry mix Mirabegron, glyceryl dibehanate, lactose and crospovidone optionally with carnauba wax & cetyl alcohol as per the formula using a high shear mixer.
2) Heat the blend at 80° C. to get a molten mass.
3) Cool the molten mass and mill it to get the granules of desired size.
4) Add lactose, butylated hydroxy toluene, crospovidone, colloidal anhydrous silica & magnesium stearate to the granules obtained in step 3 and mix using a low shear mixer.
5) Compress the granules into a tablet.
6) Dissolve wax & polyvinyl alcohol/povidone in solvent under continuous stirring.
7) Disperse talcum & titanium dioxide under continuous stirring.
8) Spray the coating solution on tablets Dissolution Data:

TABLE 2

| Dissolution Data for Examples 1 to 3 | | | | |
|---|---|---|---|---|
| Time (Hr) | Example 1 | Example 2 | Example 3 | Betmiga (Reference Product) |
| 1 | 7 | 10 | 15 | 7 |
| 3 | 20 | 35 | 20 | 25 |
| 5 | 36 | 55 | 40 | 48 |
| 7 | 46 | 75 | 67 | 71 |
| 8.5 | 53 | 82 | 80 | 86 |
| 10 | 55 | 87 | 91 | 96 |
| 12 | 59 | 92 | 98 | 99 |
| F2 Value | 28 | 58 | 62 | — |

TABLE 3

| Examples 4 to 7 | | | | |
|---|---|---|---|---|
| Material Name | Example-4 (In mg) | Example-5 (In mg) | Example-6 (In mg) | Example-7 (In mg) |
| DRY MIX | | | | |
| Mirabegron | 50.00 | 50.00 | 50.00 | 50.00 |
| Lactose monohydrate | 139.30 | 114.30 | 109.30 | 99.30 |
| Glyceryl Dibehenate | 50.00 | 50.00 | 50.00 | 50.00 |
| Sodium Lauryl sulphate | 3.00 | 3.00 | 3.00 | 3.00 |
| Povidone (PVP K30) | 2.50 | 2.50 | 2.50 | 2.50 |
| BHT | 0.70 | 0.70 | 0.70 | 0.70 |
| Solvent | Qs | Qs | Qs | Qs |
| Mannitol (Pearlitol 200SD) | 50.00 | 75.00 | 80.00 | 90.00 |
| Colloidal Anhydrous Silica | 2.00 | 2.00 | 2.00 | 2.00 |
| Magnessium Stearate | 2.50 | 2.50 | 2.50 | 2.50 |
| TOTAL | 300.00 | 300.00 | 300.00 | 300.00 |
| FILM COATING | | | | |
| Povidone/PVA | 10.5 | 10.5 | 10.5 | 10.5 |
| WAX | 1.5 | 1.5 | 1.5 | 1.5 |
| Talcum | 2.5 | 2.5 | 2.5 | 2.5 |
| Titanium dioxide | 1.5 | 1.5 | 1.5 | 1.5 |
| Solvent | Qs | Qs | Qs | Qs |
| TOTAL | 316.00 | 316.00 | 316.00 | 316.00 |

Manufacturing Procedure

1) Dry mix Mirabegron, lactose Monohydrate, Glyceryl dibehante, Sodium lauryl sulphate in High shear Mixer
2) Granulate the dry mix with granulation agent Povidone, BHT & Suitable solvent
3) Heat the blend at 80° C. Temperature till to get molted mass
4) cool the molted mass and miled to get desired size of pellets
5) Add Mannitol, Colloidal anhydrous silica & Magnesium stearate in low sheare mixer and mix
6) Compress the tablets
7) Coat the tablets Dissolution Data

TABLE 4

| Dissolution Data for Examples 4 to 7 and Reference product Dissolution medium pH 6.8 phosphate Buffer | | | | | |
|---|---|---|---|---|---|
| Time (Hour) | Test Product Example-4 | Test Product Example-5 | Test Product Example-6 | Test Product Example-7 | Betmiga (Reference Product) |
| 0 | 0 | 0 | 0 | 0 | 0 |
| 1 | 3 | 6 | 8 | 13 | 7 |
| 3 | 11 | 28 | 30 | 56 | 25 |
| 5 | 32 | 54 | 58 | 76 | 48 |
| 7 | 53 | 67 | 77 | 82 | 71 |
| 8.5 | 61 | 83 | 89 | 90 | 86 |
| 10 | 67 | 94 | 95 | 99 | 96 |
| 12 | 74 | 96 | 98 | 99 | 99 |

Stability Data (for Example 5)

TABLE 5

Test Product; Packaging style: Alu-Alu blister

| Tests | Assay Limit: | Dissolution (%) Media: 900 ml, Phosphate buffer pH 6.8, Basket, 100 RPM | | | | | | | Related Substances Impurity A | Impurity B | Impurity C | Highest Unknown Impurity | Total Impurities |
|---|---|---|---|---|---|---|---|---|---|---|---|---|---|
| Batch No/Condition | 95.0-110.0% | 1 hr | 3 hrs | 5 hrs | 7 hrs | 8.5 hrs | 10 hrs | 12 hrs | NMT 0.3% | NMT 0.3% | NMT 0.3% | NMT 0.2% | NMT 1.0% |
| Initial | 99.3% | 12 | 31 | 57 | 72 | 80 | 85 | 92 | ND | BDL | 0.05% | 0.07% | 0.18% |
| 1 M (40/75) | 98.2% | 10 | 30 | 60 | 70 | 72 | 74 | 76 | ND | BDL | 0.05% | 0.06% | 0.17% |
| 2 M (40/75) | 101.6% | 12 | 41 | 64 | 72 | 75 | 78 | 81 | ND | BDL | 0.07% | 0.06% | 0.18% |
| 3 M (40/75) | 95.6% | 9 | 42 | 70 | 77 | 80 | 83 | 85 | ND | ND | 0.04% | 0.07% | 0.18% |
| 6 M (40/75) | 97.0% | 11 | 53 | 74 | 80 | 81 | 84 | 85 | ND | ND | 0.06% | 0.07% | 0.19% |

BDL # below detectable limit
ND # not detectable

TABLE 6

Test Product; Packaging style: HDPE Bottle 30 CC

| Tests | Assay Limit: | Dissolution (%) Media: 900 ml, Phosphate buffer pH 6.8, Basket, 100 RPM | | | | | | | Related Substances Impurity A | Impurity B | Impurity C | Highest Unknown Impurity | Total Impurities |
|---|---|---|---|---|---|---|---|---|---|---|---|---|---|
| Batch No/Condition | 95.0-110.0% | 1 hr | 3 hrs | 5 hrs | 7 hrs | 8.5 hrs | 10 hrs | 12 hrs | NMT 0.3% | NMT 0.3% | NMT 0.3% | NMT 0.2% | NMT 1.0% |
| Initial | 99.3% | 12 | 31 | 57 | 72 | 80 | 85 | 92 | ND | BDL | 0.05% | 0.07% | 0.18% |
| 1 M (40/75) | 101.4% | 10 | 27 | 51 | 65 | 70 | 71 | 72 | ND | BDL | 0.06% | 0.06% | 0.18% |
| 2 M (40/75) | 103.0% | 12 | 40 | 66 | 74 | 76 | 80 | 83 | ND | BDL | 0.08% | 0.05% | 0.13% |
| 3 M (40/75) | 95.2% | 10 | 31 | 60 | 68 | 73 | 75 | 79 | ND | ND | 0.06% | 0.06% | 0.18% |
| 6 M (40/75) | 96.0% | 11 | 37 | 80 | 89 | 93 | 94 | 95 | ND | ND | 0.05% | 0.06% | 0.23% |

BDL # below detectable limit
ND # not detectable

The invention claimed is:

1. An extended release composition consisting of:

mirabegron or a salt thereof;

a release controlling agent wherein the release controlling agent consists of a non-polymeric hydrophobic excipient selected from the group consisting of glyceryl behenate, carnauba wax, cetyl alcohol, hydrogenated vegetable oil, hydrogenated castor oil and a mixture thereof; and a mixture consisting of a diluent, a binder, a surfactant, and an antioxidant wherein the release controlling agent is present in a concentration ranging from 0.5 to 50% by weight of the extended release composition; and wherein dissolution of mirabegron from the extended release composition is not less than 20% in 3 hours and not less than 50% in 7 hours when measured in vitro in USP Apparatus Type 2 (Paddle) using pH 6.8-phosphate buffer of 900 mL, at 100 rpm.

2. The extended release composition as claimed in claim 1, wherein the release controlling agent is present in a concentration ranging from 10 to 40% by weight of the extended release composition.

3. The extended release composition as claimed in claim 1, wherein the extended release composition is in the form of a tablet, a capsule, a sachet, granules, beads, pellets or a powder.

4. The extended release composition as claimed in claim 1, wherein the diluent is selected from the group consisting of mannitol, lactose, and a mixture thereof, the binder is selected from the group consisting of povidone, hydroxypropyl cellulose, starch, and a mixture thereof; the surfactant is sodium lauryl sulphate and the antioxidant is selected from the group consisting of butylated hydroxytoluene, butylated hydroxyanisole, and a mixture thereof.

5. A process for manufacturing an extended release composition of claim 1, the process consisting of:

a) dry mixing mirabegron or a salt thereof, a release controlling agent, lactose, and sodium lauryl sulphate to obtain a dry mix;

b) granulating the dry mix of step a) with a granulation agent, and butylated hydroxytoluene to obtain a blend, wherein the granulation agent is povidone;

c) heating the blend of step b) to get a molted mass;

d) cooling the molted mass, and milling to get pellets or granules;

e) mixing the granules or pellets formed in step d) and adding one or more excipients to obtain a mixture, wherein the excipients are selected from the group consisting of lactose, mannitol, butylated hydroxyl toluene, crospovidone, colloidal anhydrous silica and magnesium stearate; and f) compressing the mixture of step e) to form a tablet or fill the mixture into a capsule.

6. The process as claimed in claim 5, wherein the release controlling agents are selected from the group consisting of glyceryl behenate, carnauba wax, cetyl alcohol, hydrogenated vegetable oil, hydrogenated castor oil, and a mixture thereof.

* * * * *